(12) United States Patent
Moon et al.

(10) Patent No.: US 7,377,291 B2
(45) Date of Patent: May 27, 2008

(54) MULTIPORT ROTARY VALVE

(75) Inventors: Jim Moon, Hillsboro, OR (US); John Hinshaw, Hillsboro, OR (US); Steve Mahoney, Hillsboro, OR (US)

(73) Assignee: Serveron Corporation, Hillsboro, OR (US)

( * ) Notice: Subject to any disclaimer, the term of this patent is extended or adjusted under 35 U.S.C. 154(b) by 151 days.

(21) Appl. No.: 11/321,187

(22) Filed: Dec. 28, 2005

(65) Prior Publication Data

US 2007/0144594 A1   Jun. 28, 2007

(51) Int. Cl.
*F16K 11/06* (2006.01)

(52) U.S. Cl. .................. 137/625.46; 137/553

(58) Field of Classification Search ........... 137/553, 137/554, 625.46; 73/19.02, 864.81, 864.83
See application file for complete search history.

(56) References Cited

U.S. PATENT DOCUMENTS

| | | | |
|---|---|---|---|
| 3,040,777 A | 6/1962 | Carson et al. | |
| 3,223,123 A * | 12/1965 | Young | 137/625.46 |
| 3,297,053 A | 1/1967 | McKinney | |
| 3,422,848 A | 1/1969 | Liebman et al. | |
| 3,975,946 A | 8/1976 | Ball et al. | |
| 4,030,369 A * | 6/1977 | Etheridge | 73/863.33 |
| 4,158,630 A | 6/1979 | Stearns | |
| 4,486,001 A | 12/1984 | Santefort | |
| 4,550,742 A | 11/1985 | Stearns | |
| 4,554,942 A | 11/1985 | Williams et al. | |
| 4,625,569 A * | 12/1986 | Toei et al. | 73/863.72 |
| 4,807,662 A * | 2/1989 | Verne | 137/554 |
| 4,957,008 A * | 9/1990 | Proni et al. | 73/864.83 |
| 4,962,871 A | 10/1990 | Reeves | |
| 6,098,646 A * | 8/2000 | Hennemann et al. | 137/101.19 |
| 6,193,213 B1 | 2/2001 | Stearns | |
| 6,202,698 B1 | 3/2001 | Stearns | |
| 6,537,451 B1 | 3/2003 | Hotier | |
| 6,719,001 B2 | 4/2004 | Ahlgren et al. | |
| 6,779,557 B2 | 8/2004 | Weiss | |

* cited by examiner

*Primary Examiner*—John Fox
(74) *Attorney, Agent, or Firm*—Hancock-Hughey LLP

(57) ABSTRACT

A multiport rotary valve has a stator with plural flow paths and a rotary valve plate having plural flow channels. The rotary valve plate defines a rotor that rotates relative to the stator to define unique plural fluid pathways from the stator, through the valve plate, and returning through the stator. Rotation of the rotary valve plate is controlled by a microprocessor, which includes an optical sensor to determine the position of the rotor.

9 Claims, 9 Drawing Sheets

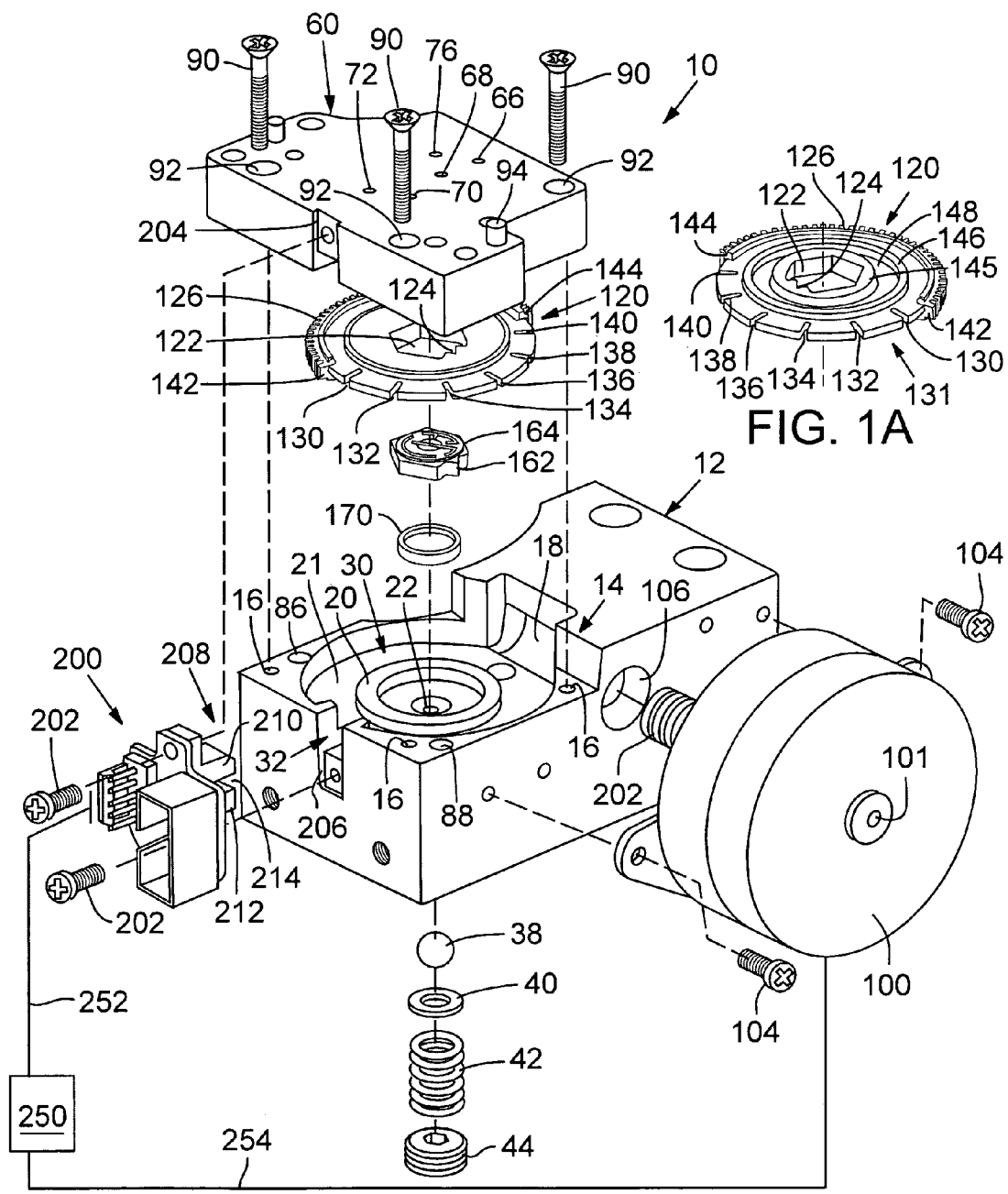

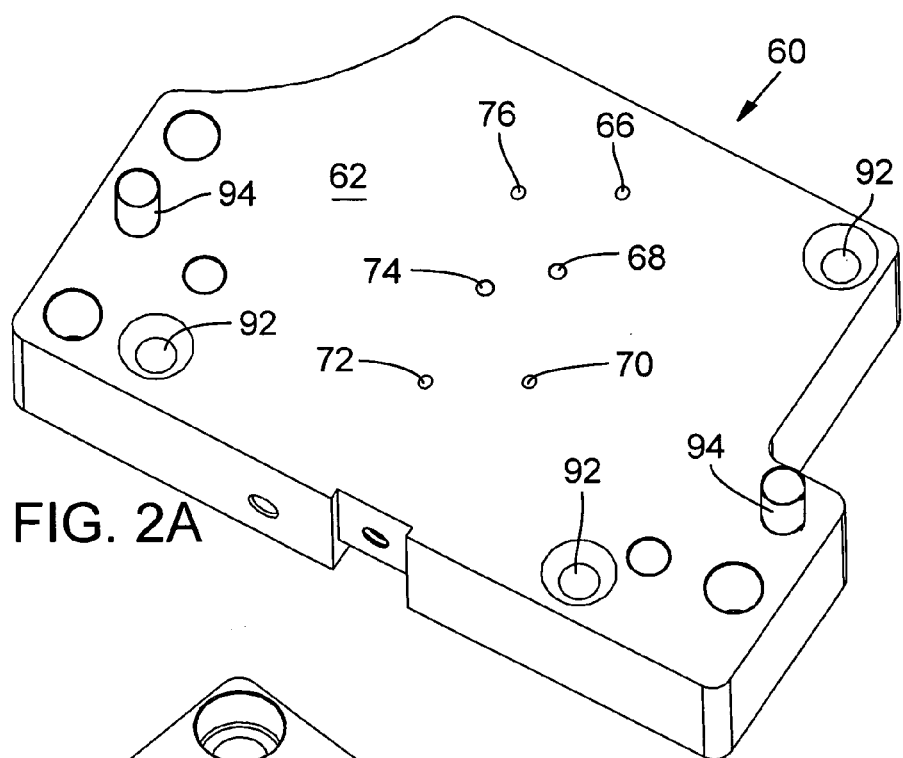
FIG. 2A
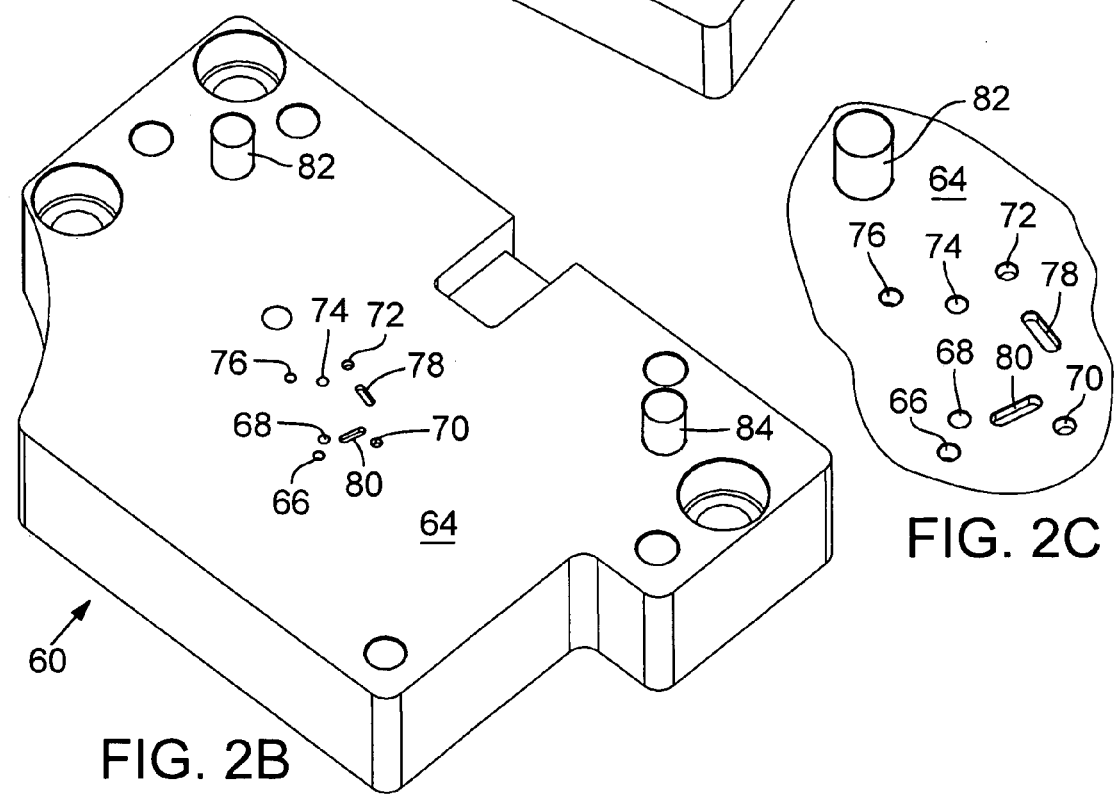
FIG. 2B
FIG. 2C

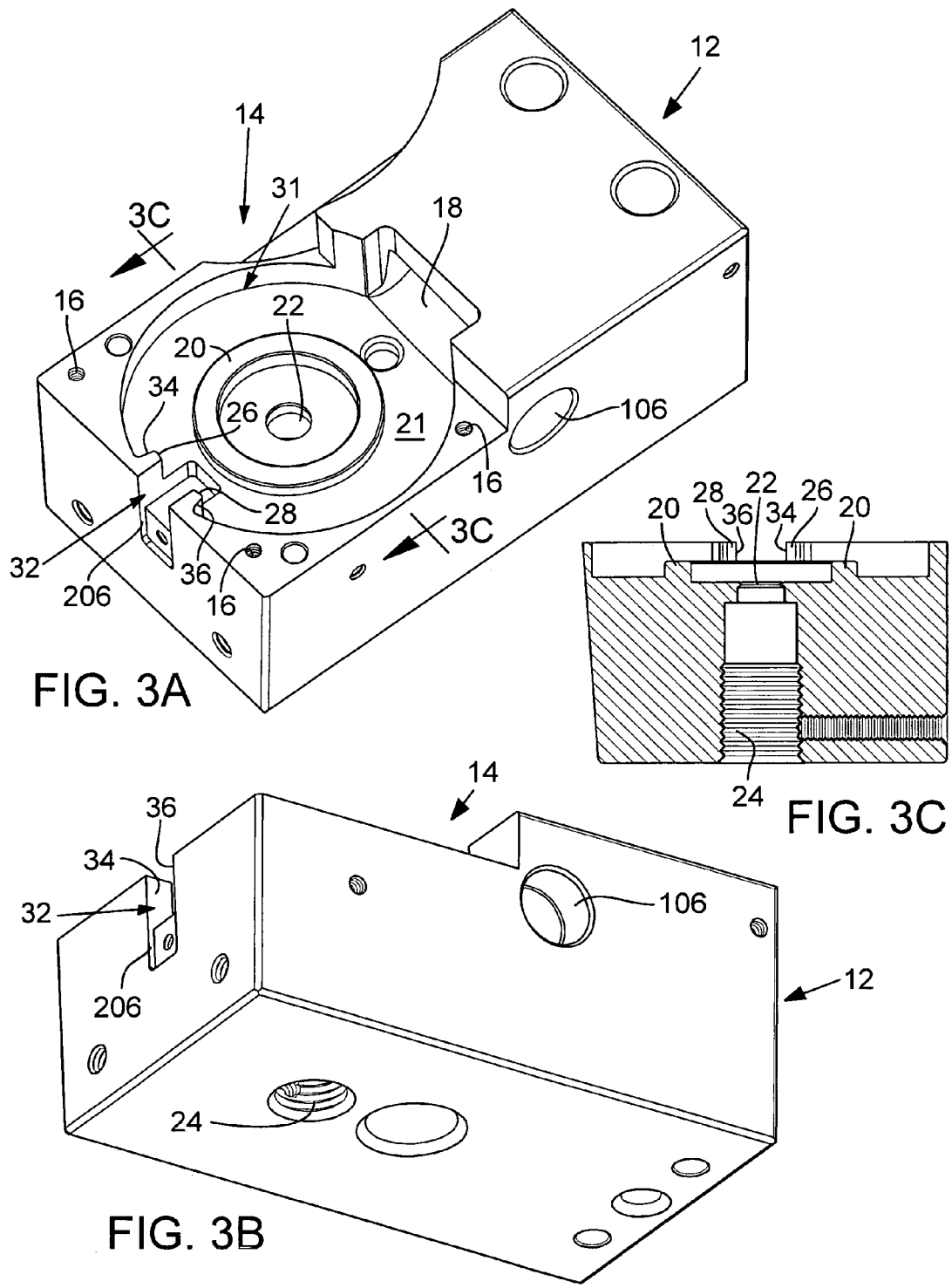

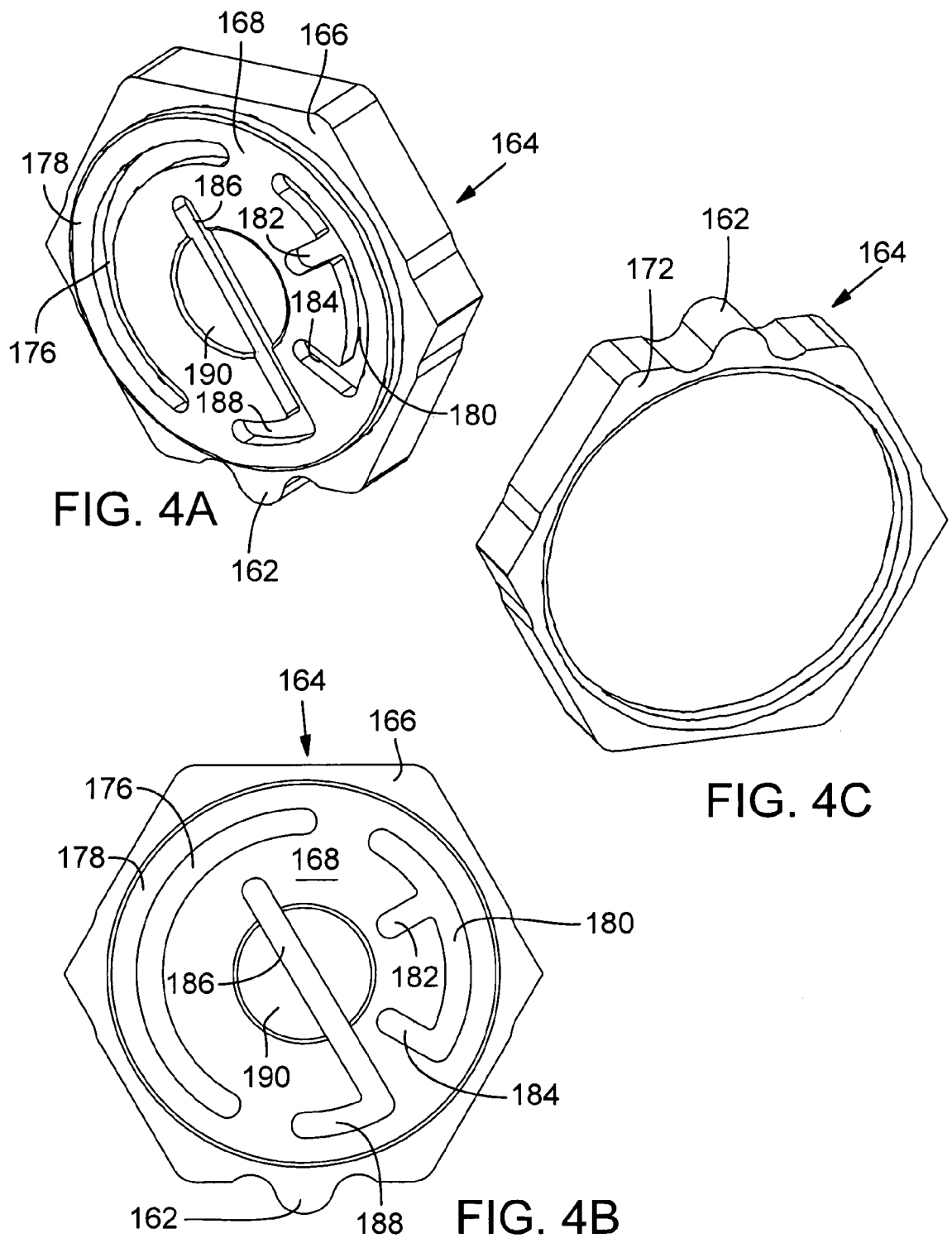

VENT EXIT

MULTIPORT ROTARY VALVE

FIELD OF THE INVENTION

The present invention relates to devices and methods for directing and controlling the flow of multiple fluids to and within analytical instruments, and more specifically, a rotary valve having multiple ports for use with instruments such as gas chromatographs.

BACKGROUND

Many chemical analytical instruments rely upon controlled and accurate fluid flow through the instrument during analytical processing. Such instruments include machines designed to perform chemical analysis of various types, purify samples and to perform monitoring of various aspects of laboratory and commercial processing. To name just a few of the types of analytical instruments in which precise fluid flow is a critical part of the functioning of the machines, there are chromatographs of numerous types such as gas chromatographs (GCs) and liquid chromatographs (LCs), spectrophotometers of many kinds, and many other similar instruments. Gas chromatographs, for example, rely upon accurate control and processing of known quantities of gas flowing through separation columns during the analytical processing. The accuracy and precision of analytical results depend directly on accurate and precise fluid flow. Accordingly, without accurate control of fluid flow, analytical results are compromised.

In a GC the sample is in the form of gas. Samples of fluid under test are typically under the control of control devices such as pumps, valves, pressure transducers and pressure regulators. The control devices help in the acquisition of samples, and the isolation, handling and separation of the samples during the process of chemical analysis. In a chromatograph, a sample aliquot is directed, either manually or automatically, through a complicated array of plumbing hardware and control systems that perform various functions before the sample flows through one or more separation columns and detectors. In the separation columns different compounds in the sample fluid are isolated as a result of specific physico-chemical interactions with the separation materials contained within the column while under flow. As the isolated compounds flow out of the columns they flow through detectors of various kinds that assist in identifying and quantifying the compounds.

In a chromatograph the fluid flow and control systems must accommodate several other fluids in addition to sample fluids. These include carrier and calibration fluids, which must be routed in very specific precisely and accurately controlled flow paths through the instrument.

It is obvious that in many analytical instruments that require controlled fluid flow there are numerous fluid flow paths, and complex hardware systems that include tubing, couplings, valves, sensors, pumps and regulators of various kinds. The plumbing systems in even relatively simple instruments such as some chromatographs can become exceedingly complicated, not to mention the complexity added by the fluid control systems.

There are a variety of different kinds of valves used in analytical instruments such as chromatographs in order to direct and control fluid flow. Among these are binary valves, rotary valves, and slide valves, and combinations of these. In addition, there are multiple binary valves such as two and three-way binaries, which may be connected in various combinations to simultaneously direct fluid flow through single or multiple flow channels. Rotary valves, diaphragm valves and slide valves, both dual and multi-position, are used to direct fluid flow through multiple ports and channels that are arranged in either a circular or linear orientation.

Precision, reliability, repeatability, reproducibility and accuracy are of course primary goals of any such analysis. As such, it is essential in an analytical instrument to eliminate, or at least minimize, all sources of system failure that may detract from these goals or might lead to problems such as leaking fittings that can adversely effect the analytical processing. The complexity of the plumbing and fluid controlling hardware of many analytical instruments presents a situation that is at odds with the fundamental principles of accuracy and precision that such instruments rely upon. Accurate precise, repeatable and reproducible analytical results require correspondingly accurate, precise, repeatable and reproducible fluid processing, without system failures such as non-fluid-tight couplings. But every fitting, connection, interconnection and fluid-controlling device in an analytical instrument introduces a potential site for a problem such as a leak. When even a small leak occurs in a critical connection the accuracy, precision, repeatability and reproducibility of analytical test data is compromised. In an instrument that contains dozens of couplings and connections the opportunity for incorrectly connected fittings is multiplied many times over.

The problems described above with respect to complicated fluid connections are well known to any laboratory technician who has operated an analytical instrument such as those described. Even in the relatively idealized conditions of a modern laboratory, and even with laboratory grade instruments, plumbing problems are a constant source of trouble with analytical instruments such as chromatographs. As such, there is a great benefit in reducing the number and complexity of fittings in an instrument that uses fluid flow.

But the problems noted above are even more pronounced with analytical instruments that are designed for use in the field rather than in a controlled laboratory environment. There are several reasons. First, field instruments tend to be smaller since portability may be a primary goal. As the instruments get smaller so do the fittings and connections. Miniaturized hardware mandates reduced fluid flow rates, and it becomes correspondingly difficult to ensure fluid-tight processing. Second, an instrument designed for use in the field is often subject to more extreme environmental conditions and rougher handling. In many respects, therefore, field units need to be even more robust than their laboratory counterparts. This can be a difficult objective when another goal in designing the unit is reduction of size.

The problems described above with complicated plumbing, control and hardware systems are amplified many times over under field conditions of extreme hot or cold environments. Extreme temperature variations can cause thermal expansion and contraction that leads to leaking fittings and other connections. In addition, environmental vibrations can, over time, loosen fittings and damage sensitive connections.

Therefore, despite advances in the technological solutions surrounding analytical instruments designed to sample, analyze and report data from remote locations, there is a need for a fluid handling system that is rugged and redundant enough that it will function without failure and without regular maintenance. There is a further need for a fluid handling system that uses small quantities of fluid so that it may be used with miniaturized instruments. Such a fluid handling system would be advantageously and beneficially used in both field instruments and in laboratory grade instruments.

The present invention relates a multiport rotary valve that in a preferred embodiment has six separate external ports. The valve simplifies fluid handling systems by replacing a relatively large number of individual two and three-way binary valves or conventional rotary valves that would be required to do the same fluid handling. The invention greatly reduces the number of active components in the fluid handling system, including tubing, fittings, junctions, etc., and thereby decreases the number of possible failure points—i.e., leaks, mechanical and electrical failure points. The rotary valve of the present invention improves reliability and provides positive positional feedback that greatly improves error and failure detection, and the valve reduces material assembly costs. Finally, the valve according to the present invention minimizes interconnecting volumes between system components, which minimizes the amount of fluid cross-contamination and mixing between various components of the system. This improves both accuracy and precision of analytical results.

BRIEF DESCRIPTION OF THE DRAWINGS

The invention will be better understood and its numerous objects and advantages will be apparent by reference to the following detailed description of the invention when taken in conjunction with the following drawings.

FIG. 1 is a perspective exploded view of a multiport rotary valve assembly according to the present invention illustrating the components of the assembly. The valve assembly shown in FIG. 1 is a six port valve.

FIG. 1A is a perspective view of the lower side of the gear component of the valve assembly shown in FIG. 1.

FIG. 2A is a perspective view of the upper or outer surface of the stator shown in FIG. 1.

FIG. 2B is a perspective view of the lower or inner surface of the stator shown in FIG. 2A.

FIG. 2C is an enlarged view of the flow channels and bores in the lower surface of the stator shown in FIG. 2B, shown in isolation.

FIG. 3A is a top perspective view of the valve housing of the valve assembly shown in FIG. 1.

FIG. 3B is a bottom perspective view of the valve housing shown in FIG. 3A.

FIG. 3C is a cross sectional view of the valve housing of FIGS. 3A and 3B, taken along the line 3-3 of FIG. 3A.

FIG. 4A is a top perspective view of the six port rotor used with the valve assembly of FIG. 1.

FIG. 4B is a top plan view of the rotor shown in FIG. 4A.

FIG. 4C is a bottom perspective view of the rotor show in FIG. 4A.

FIG. 6 shows the valve rotor in a first rotational position in which fluid is circulated from an extractor to a GC sample loop.

FIG. 7 shows the valve rotor in a second rotational position, which is used for sample aliquot isolation in the GC sample loop prior to sample injection.

FIG. 8 shows the valve rotor in a third rotational position in which fluid from the GC side of the valve is vented to atmosphere.

FIG. 9 shows the valve rotor in a fourth rotational position, which allows calibration gas to be isolated in the GC sample loop prior to sample injection.

FIG. 10 shows the valve rotor in a fifth rotational position, in which calibration gas flows through the GC loop.

FIG. 11 shows the valve rotor in a sixth rotational position, which is an extractor loop pump out position.

DETAILED DESCRIPTION OF THE PREFERRED EMBODIMENTS

Figure 5:
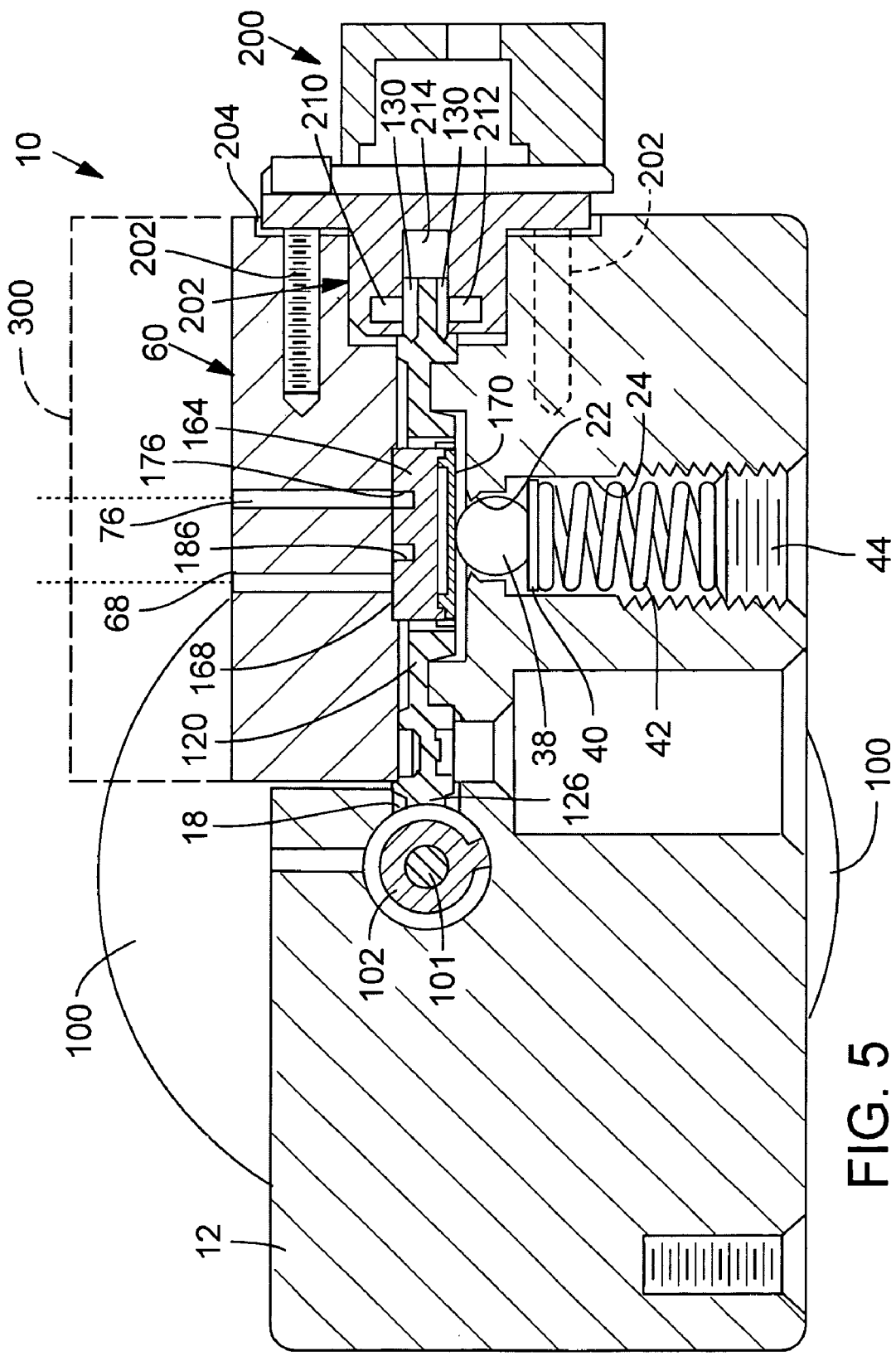
FIG. 5 is a cross sectional view through the valve assembly shown in FIG. 1, in which all of the components shown in FIG. 1 have been assembled.

A preferred embodiment of a multiport rotary valve assembly 10 according to the present invention is shown in an exploded view in FIG. 1. The valve assembly 10 comprises several primary components, including a housing 12, a stator 60 that is mounted to the housing, a gear 120 that seats a rotor assembly 160 between the stator 60 and housing 12, an optical sensor assembly 200 and a drive motor 100. Valve assembly 10 is under the control of a microprocessor 250. Each of these primary components is described in detail below, as are the subcomponents that are used in each primary component, and the manner in which they are assembled and operated. It will be appreciated that the valve assembly 10 shown in the drawing figures and described herein is especially suited for use in routing and controlling fluid flow in analytical instruments such as gas chromatographs and the like. Accordingly, as explained in detail with respect to the series of semi-schematic illustrations of FIGS. 6 through 11, the valve assembly 10 is used in conjunction with various fluid sources and fluid pathways. In particular, in the present embodiment the valve assembly is connected to a sample source, and a source of a calibration gas, to a gas chromatograph and to vents. The valve assembly 10 controls fluid flow and routes fluid from the sample source and calibration gas to and from the GC and the vents.

Each of the individual components will be described generally first. With reference to FIG. 1 and FIGS. 3A through 3C, housing 12 serves as a base to which the various other primary components of valve assembly 10 are mounted. Housing 12 includes various threaded openings positioned for attaching the other components, as detailed below. The housing is preferably machined from a unitary piece of material such as metal.

Stator 60 is fixedly mounted to housing 12 and includes various bores that define fluid pathways that communicate with rotor assembly 160 to define the rotary valve system. With reference to FIGS. 1 and 2A, stator 60 is a monolithic block of material sized and configured to be seated in a cooperatively shaped and configured seat area 14 defined in housing 12. Stator 60 has an upper surface 62 (FIG. 2A) and a lower surface 64 (FIG. 2B) and plural bores through the stator that define fluid pathways therethrough. Specifically, as shown in FIG. 2A, there are six bores, 66, 68, 70, 72, 74 and 76 that are spaced around a central portion of the upper surface 62 of stator 60. The bores extend completely through the stator and thus define fluid pathways through the stator, extending from the upper surface 62 to the lower surface 64. The bores are arranged relative to one another at the upper surface in a first orientation, and at the lower surface in a second orientation that is different from the first orientation. With reference to FIG. 2B, which shows the lower surface 64, the positions of bores 66, 68, 70, 72, 74 and 76 may be seen. It will be appreciated by comparison of FIGS. 2A and 2B that the relational spacing and arrangement of the bores in upper surface 62 is thus different from the spacing and arrangement of the bores where they terminate in lower surface 64. As detailed below, the arrangement of the bores in lower surface 64 is cooperative with flow channels formed in rotary assembly 160 so that various fluid flow paths may be defined, opened and closed as the rotor assembly rotates. The bores are preferably formed by drilling the stator. It will also be appreciated that some or all of the bores are drilled at angles relative to the other bores, and that not all of the bores are perpendicular to the plane defined by upper and lower surfaces 62 and 64.

In addition to the bores described above, which extend completely through stator 60, two short, closed-ended or blind grooves or channels 78 and 80 are formed in lower surface 64 of stator 60. With reference to FIG. 2C, bores 66 through 76 define through holes that extend completely through the stator, whereas channels 78 and 80 are formed only partly into the lower surface 64 of the stator. The function of the blind channels 78 and 80 is detailed below.

As shown in FIG. 1, stator 60 is mounted to housing 12 such that lower surface 64 of the stator faces the housing. Alignment pins 82 and 84 extend out of lower surface 64 and, when the stator 60 is mated to housing 12, alignment pins 82 and 84 enter cooperatively sized and placed bores 86 and 88 formed in the periphery of seat area 14 of housing 12. Screws 90 extend through through-holes 92 formed in stator 60 and thread into threaded openings 16 around the periphery of seat area 14 to anchor stator 60 firmly in place on housing 12. Alignment pins 94 extend upwardly from upper surface 62 of stator 60. As detailed below, alignment pins 94 serve to align a manifold (FIG. 12) that mates against the upper surface of the stator.

Gear 120 is shown in FIGS. 1 and 1A. The gear defines a central hexagonal opening 122 that is configured to receive and seat rotor assembly 160, which is cooperatively hexagonally shaped. Hexagonal opening 122 includes a notch 124 that cooperates with a tab 162 formed on rotor assembly 160 so that the rotor assembly is always positioned correctly in opening 122. Gear 120 generally defines a round disk that has gear teeth 126 that extend approximately 180° around the outer periphery of the disk. The peripheral section of gear 120 that is defined by gear teeth 126 terminates in opposite shoulders 142 and 144 that are about 180° opposite one another. The function of shoulders 142 and 144 is to limit the rotation of gear 120 in housing 12, as detailed below.

The peripheral edge of gear 120 opposite gear teeth 126 comprises a slotted peripheral portion 131 comprising a series of six slots 130, 132, 134, 136, 138 and 140 that extend from the peripheral edge of the disk inwardly a short distance toward the center of the disk. Slots 130 through 140 are at evenly spaced intervals around the slotted peripheral portion 131 of gear 120 opposite gear teeth 126.

The lower side of gear 120 is shown in FIG. 1A, and includes a pair of raised, concentric and spaced apart circular walls 145 and 146 encircling hexagonal opening 122; circular wall 145 is nearer opening 122. The two walls 145 and 146 define a circular groove 148 therebetween.

Drive motor 100 is a reversible electrical stepper motor having a drive shaft 101 (FIG. 5) with a worm gear 102 at the end of the shaft. Drive motor 100 is mounted with screws 104 to housing 12 with the drive shaft extending into an opening 106 in housing 12. When the drive motor 100 is secured to housing 12, worm gear 102 communicates with an opening 18 in seat area 14 of housing 12, and as detailed below, worm gear 102 meshes with gear teeth 126 so that rotation of the drive shaft of motor 100 rotates gear 120.

Rotor assembly 160 will now be described with reference to FIG. 1 and FIGS. 4A through 4C. The rotor assembly is the combined valve plate 164 and pressure plate 170. Valve plate 164 has a hexagonally shaped outer peripheral edge that as noted above includes a tab 162 that mates with a notch 124 in central hexagonal opening 122 of gear 120. Valve plate 164 is preferably fabricated from a plastic such as a acetal-based material such as a Delrin, although other materials will suffice. The materials used to fabricate the valve plate and stator are selected so that a fluid-tight seal may be formed between the two, as detailed below.

The upper surface of valve plate 164 is planar and is referred to as surface 166. Inwardly of the hexagonal peripheral edge of surface 166 is a raised circular section defined as planar upper surface 168. A circular pressure plate 170 is attached to the lower surface 172 of rotor assembly 160 (FIG. 1). Pressure plate 170 is preferably metallic, such as stainless steel, and is mounted to the lower surface 172.

A series of flow channels is formed in the raised upper surface 168 of upper surface 166 of valve plate 164. The flow channels are formed in the surface of the valve plate and, when stator 60 is mounted in housing 12, cooperate with bores 68 through 76 in the lower surface 64 of the stator to define controlled fluid pathways through the valve assembly 10. Specifically, with reference to FIGS. 4A and 4B, there are three flow channels formed in valve plate 164. First flow channel 176 is an arcuate, non-branched channel that extends around one peripheral edge section 178 of raised upper surface 168. Generally opposite first flow channel 176 is second flow channel 180, which also is generally arcuate and which includes two inwardly extending branch channels, referred to as first and second branches 182 and 184, respectively. As shown in FIG. 4B, first flow channel 176 and second flow channel 180 combine to form dual concentric flow channels in the valve plate 164. The function of these dual concentric channels is detailed below. Bisecting between the first and second flow channels 176 and 180 is the third flow channel 186. Third flow channel 186 extends across the center of raised circular section 168 and at one outer end includes an arcuate section 188, so that the third flow channel is generally L-shaped. A slightly recessed circular depression 190 is formed around a center portion of the valve plate 164 so that the third flow channel bisects circular depression 190. As shown in FIG. 4A, the depth of circular depression 190 is less than the depth of the first, second and third flow channels, 176, 180 and 186.

The final primary component that comprises multiport rotary valve assembly 10 is optical sensor assembly 200, which mounts with screws 202 to cooperatively formed notches 204 and 206 formed respectively in stator 60 and housing 12. Reference is made to FIGS. 1 and 5. Optical sensor assembly 200 includes an optical sensor shown generally at 208 that is capable of transmitting a beam of light between an upper optical receptor 210 and a lower optical transmitter 212. Optical receptor 210 and optical transmitter 212 are spaced apart to define a slot 214 therebetween. When sensor assembly 200 is mounted to housing 12 and stator 60, optical sensor 208 extends into seat area 14 so that the slotted peripheral portion 131 of gear 120, which as noted above includes slots 130 through 140, extends into slot 214 of optical sensor assembly 200.

Rotary valve assembly 10 is used with appropriate control electronics that are shown schematically in FIG. 1 as microprocessor 250. The microprocessor 250 is operatively connected to both optical sensor 208 and drive motor 100, shown schematically with data wires 252 and 254, respectively, so that both the sensor and drive motor are operated by and under the control of the microprocessor. It will be appreciated that the word microprocessor is used generically herein for a programmed device capable of controlling operations of rotary valve assembly 10, and includes other appropriate hardware and software, input interfaces, and optional telephony for remote operation.

Turning now to FIGS. 1, and 3A through 3C, housing 12 will be described in detail. As noted above, housing 12 defines a seat area 14 that is configured for receiving and mounting stator 60, gear 120 and rotor assembly 160. Seat area 14 includes a generally circular, depressed center section 30, the circumference of which is slightly larger than the circumference of gear 120 so that the gear is held within the depressed center section 30. A raised circular ring 20 extends upwardly from the floor 21 of seat area 14, and an opening 22 extends through floor 21 at the center of circular opening 20. As best seen in the sectional drawing of FIG. 3C, opening 22 opens into a cylindrical opening 24 that has a larger diameter than opening 22. The lower portion of opening 24 is threaded. A notch 32 is cut through a side portion of housing 12 to define a slot for receiving optical sensor assembly 200, and includes inwardly extending tabs 26 and 28 that define shoulders 34 and 36 on either side of notch 32.

With returning reference to FIG. 1, a ball bearing 38, the diameter of which is greater than the circumference of opening 22, is held in cylindrical opening 24 by a washer 40. A spring is inserted into opening 24 and the ball bearing, washer and spring are retained under pressure in opening 24 with a nut 44 that threads into the lower portion of opening 24. It will be appreciated that there are numerous biasing structures available to provide the required mechanical pressure, including the spiral spring shown in the drawings as spring 42, and equivalent structures such as stacked Belleville spring washers and the like.

The primary components of rotary valve assembly 10 described above are assembled together as generally shown in FIGS. 1 and 5. More specifically, drive motor 100 is secured to housing 12 with screws 104 so that drive shaft 101 extends into housing 12 through opening 106 and worm gear 102 communicates with seat area 14 through opening 18. Rotor assembly 160 (which is the combination of the valve plate 164 assembled with pressure plate 170) is inserted into hexagonal opening 122 of gear 120 as shown in FIG. 1. As noted, rotor assembly 160 is keyed with notch 124 and tab 162 in hexagonal opening 122 so the rotor assembly may be inserted into gear 120 in only one orientation. Gear 120 is then fitted in the depressed center section 31 of housing 12 such that raised circular ring 20 fits into circular groove 148 in the gear, and with shoulder 142 abutting shoulder 34. When gear 120 is mounted in this manner in housing 12, the teeth of worm gear 102 mesh with teeth 126 of gear 120. It will be appreciated that the hexagonal configuration of the valve plate and opening 122 of gear 120, in combination with notch 124 and tab 162 may be replaced with any number of geometric and structural configurations that permit only one desired orientation of the valve plate relative to the gear when the two are assembled.

Gear 120 may be rotated on the raised circular ring 20 of housing 12 by operation of motor 100 between the two end positions: the first rotational end position is defined as the point where shoulder 142 abuts shoulder 34; and the second rotational end position is defined as the point where shoulder 144 abuts shoulder 36. It will be appreciated that the gear 120 may thus rotate through about 180°.

Optical sensor assembly 200 is next mounted on housing 12. When the assembly 200 is mounted on housing 12, the optical sensor 208 extends into slot 32 in the housing such that the slotted peripheral edge 131 of gear 120 extends into slot 214 between optical receptor 210 and optical transmitter 212. Accordingly, a light beam transmitted from optical transmitter 212 toward optical receptor 210 either is unimpeded, as when the light beam extends through a slot such as slot 130 in gear 120, or is broken, as when gear 120 is in a position such that the solid portion of gear 120 between the slots interrupts the beam. When gear 120 is in the first stop position—when shoulder 142 abuts shoulder 34, slot 130 is directly over the beam of light transmitted from optical transmitter 212 to optical receptor 210, so that the beam is uninterrupted. When gear 120 is in the second stop position—when shoulder 144 abuts shoulder 36, slot 140 is directly over the beam of light from transmitter 212 to receptor 210. This interruption of the light beam as gear 120 rotates allows microprocessor 250 to calculate the relative rotational position of the gear, and hence determine the desired flow paths that are opened, or closed.

In addition, each slot 130 through 140 covers more than one rotational position of the rotor. Stated another way, under the control of microprocessor 250, motor 100 may be stopped at any point where the beam of light is transmitted through a slot. Thus, the rotor is turned as the beam of light is transmitted through a slot until the other side of the slot is reached. At this point, when the optical beam is interrupted, the rotation of the rotor may be reversed and the rotor may be rotated in the opposite direction until the beam of light is centered in the slot or is at some other desired position in the slot. This helps ensure that the position of the rotor relative to the stator is precisely as desired, which in most instances is with the light beam in the center of the slot. Also, the individual slot positions are calibrated by microprocessor 250 at startup of the valve assembly 10 so that the microprocessor will have data reflecting the exact position and width of the slots, rather than assuming that the slots are evenly spaced from one another, and of even width. This calibration step is accomplished by the rotor being rotated fully in one direction, and then fully back in the other direction with the optical beam on. As this rotation occurs, the microprocessor receives data input from the optical sensor assembly 100 that is processed in microprocessor 250 into a precise calibration map of the position and widths of the slots. This information is saved for the rotor that is being used so that with any particular rotor, the precise position and width of the slots is know. The microprocessor may perform the back and forth rotation of the rotor as a calibration step as many times as necessary to verify the calibration.

Stator 60 is next mounted in seat area 14 of housing 12, with aligning pins 82 and 84 entering bores 86 and 88, and screws 90 extending through openings 92 in stator 60 and threaded into threaded openings 16 in housing 12.

Ball bearing 38 is next inserted into opening 24, followed by washer 40 and spring 42. These are held in place in opening 24 by threading nut 44 into the opening. Nut 44 is threaded into the opening a sufficient distance to compress spring 42, which pushes against washer 40 thereby putting pressure on ball bearing 38. With reference to FIG. 5, and as noted above, the diameter of ball bearing 38 is somewhat smaller than the diameter of opening 22. Accordingly, ball bearing 38 is urged upwardly against pressure plate 170 of rotor assembly 160, thereby driving the entire rotor assembly upwardly against lower surface 64 of stator 60 so that the upper surface 168 of valve plate 164 bears against the lower surface of the stator. Both the upper surface of the valve plate and the lower surface 64 of the stator are planar. The amount of spring force applied against ball bearing 38, and thus rotor assembly 160 is sufficient to define a fluid seal between the lower surface 64 of stator 60 and the planar upper surface 168 of valve plate 164.

When the valve assembly is fully assembled, all of the bores defined in the lower surface 64 of stator 60 are located within the bounds of the perimeter of the valve plate 164 defined by the raised, circular upper surface 168 of the valve plate.

As may be seen in FIG. 5, and as detailed below, as the valve plate is rotated under the control of microprocessor 250, the various channels and branch channels in the valve plate align with, and/or come out of alignment with, the various bores through the stator. As a bore through the stator aligns with a channel in the valve plate a fluid pathway is established from the bore to the channel. When a second bore is also aligned with the same channel, a complete fluid pathway is established from a first bore in the stator, through a channel in the valve plate, and out of a second bore in the stator. The stator thus serves as the flow channel to the valve plate, and the flow channel out of the valve plate, thereby minimizing the number of fittings and connections. As the valve plate is rotated so that a bore is no longer aligned with a channel and the bore instead aligns with a flattened portion of the upper surface 168 of valve plate 164, the fluid pathway through that bore is closed where the opening in the stator meets the planar valve plate. In FIG. 5, gear 120 has been rotated to the point where bore 76 in stator 60 is aligned with channel 176 in valve plate 164, and thus has established a fluid pathway through the stator into the valve plate. Similarly, bore 68 is not aligned with a channel in the valve plate, and accordingly, there is a fluid seal at the interface between the lower extent of the bore and the upper surface of the valve plate.

Once the multiport rotary valve assembly 10 is assembled as described above, the electronic control systems defined by microprocessor 250 are connected.

Figure 12:
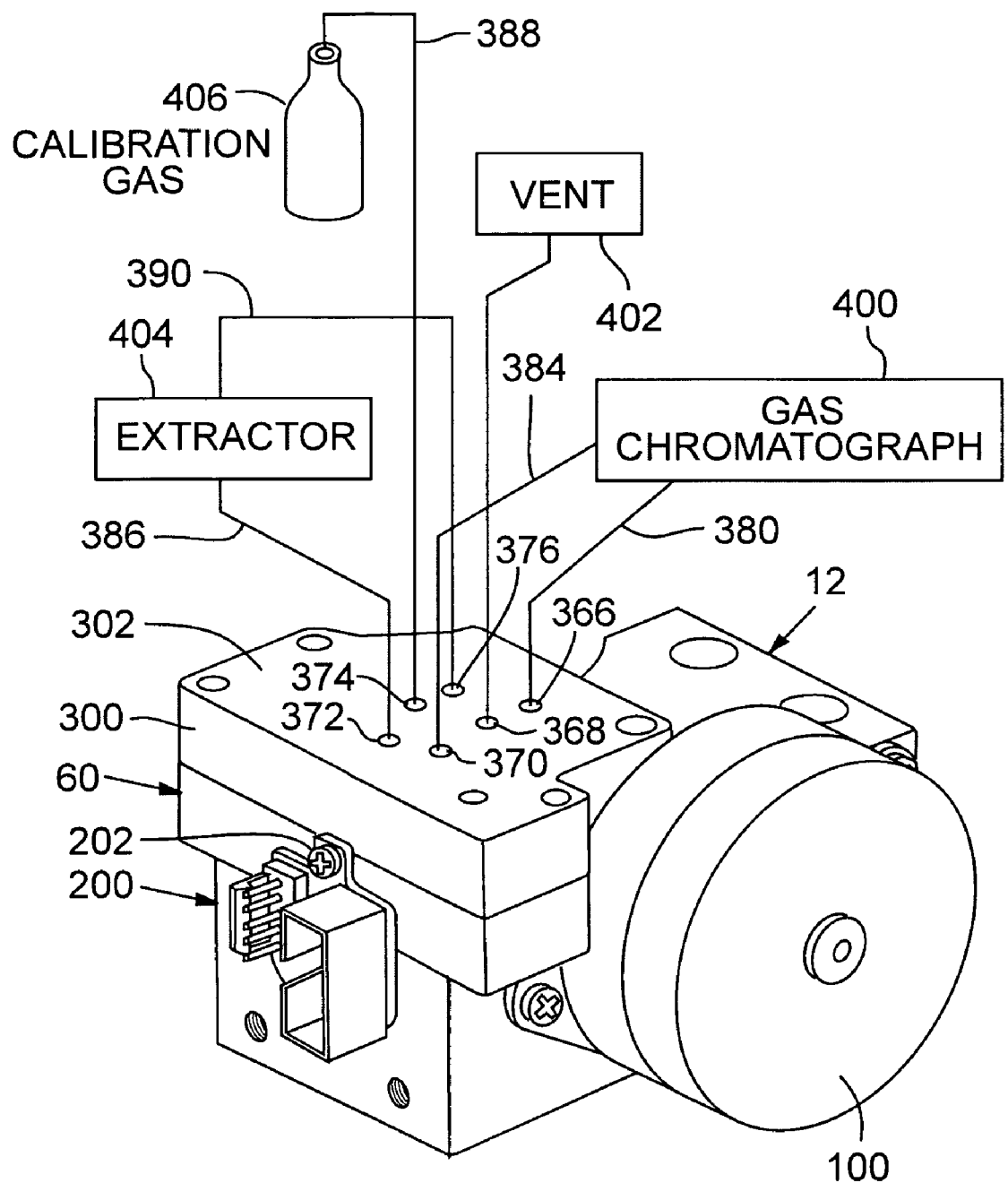
FIG. 12 is a perspective and semi-schematic view of the assembled multiport rotary valve assembly according to the present invention with a manifold connected to the stator and showing schematically the interconnections between the fluid supplies and routing components such as a GC and a source of calibration gas.

As noted above, a manifold is attached to the upper surface 62 of stator 60. With reference now to FIG. 12, the manifold 300 mates flush with and is attached to the upper surface 62 of stator 60. Manifold 300 has six bores extending from the top surface 302, with each of the bores positioned in the manifold such that when it is attached to stator 60, the bores align with the corresponding bores in the upper surface 62 of stator 60. More specifically, as shown in FIG. 12, manifold 300 has six bores, 366, 368, 370, 372, 374 and 376, each of which corresponds to and aligns with a corresponding bore through the stator 60. Although not illustrated, an O-ring gasket is interposed between the stator 60 and manifold 300 around each aligned bore to form a gas-tight seal between the manifold and stator. Thus, bore 366 aligns with and forms a fluid channel into bore 66 in stator 60; bore 368 aligns with and forms a fluid channel into bore 68 in stator 60; bore 370 aligns with and forms a fluid channel into bore 70 in stator 60, and so on. Bore 366 is ultimately connected to GC 400 with tubing 380 and is the return line from the GC. Bore 368 is ultimately connected through tubing 382, which preferably includes a frit restrictor 402, and serves as a vent. Bore 370 serves as the supply line to GC 400 through tubing 384. Bore 372 is the inlet into valve assembly 10 from extractor unit 404, via tubing 386.

Bore 374 is the inlet into valve assembly 10 from calibration gas supply, via tubing 388. And finally, bore 376 ultimately connects through tubing 390 to the inlet side of extractor 404. FIG. 12 is partially schematic in that it does not illustrate additional manifolds to which manifold 300 is attached, and which defines the fluid pathways to GC 400, etc. In other words, the various tubing components shown in FIG. 12 are actually comprised of fluid pathways through manifolds and the like, and are shown schematically in FIG. 12 and being external fluid pathways.

Extractor 404 is shown generically and may be any suitable type of extraction unit, such as a unit designed to extract gas from fluids. It will be appreciated that while an extractor is described herein, there are numerous other fluid sample sources for analysis by an analytical instrument of the type that could use the multiport rotary valve according to the present invention.

A fluid seal is formed around the outlet of each bore at the lower surface of the manifold 300 and the inlet in the corresponding bore in the upper surface 62 of the stator 60 with, for example, O-ring seals that encircle each of the aligned bores when the manifold is connected to the stator.

Operation of the fully assembled multiport rotary valve assembly 10 will now be described with specific reference to the semi-schematic illustrations of FIGS. 6 through 11. When the valve assembly 10 is assembled and microprocessor 250 operational, the rotational position of gear 120 is determined through optical sensor assembly 200. Specifically, a beam of light is transmitted from optical transmitter 212 toward optical receiver 210. Simultaneously, motor 100 is activated to turn drive shaft 101 and worm gear 102. Worm gear 102 meshes with teeth 126 of gear 120, causing gear 120 to rotate. Depending upon the initial position of gear 120 when this sequence begins, and where shoulders 142 and 144 are positioned relative to shoulders 34 and 36, the amount of rotation will be determined. As noted previously, when gear 120 is in the first stop position—when shoulder 142 abuts shoulder 34, slot 130 is directly over the beam of light transmitted from optical transmitter 212 to optical receptor 210, so that the beam is uninterrupted. Likewise, when gear 120 is in the second stop position—when shoulder 144 abuts shoulder 36, slot 140 is directly over the beam of light from transmitter 212 to receptor 210. Thus, when gear 120 rotates to the point where shoulder 142 abuts shoulder 34, the light beam passes unimpeded through slot 130 and motor 100 stops. When gear 120 rotates fully to the second stop—that is, the point where shoulder 144 abuts shoulder 36, light beam passes unimpeded through slot 140 and the motor stops.

As gear 120 rotates between the two stop positions, the slotted peripheral portion 131 of gear 120 passes between the optical transmitter 212 and optical receiver 210. As such, the beam of light between the transmitter and receiver is either uninterrupted, as when a slot such as slot 130 is directly over the path of the light beam, or is interrupted, as when a solid portion of gear 120 between slots interrupts the light beam. As gear 120 rotates the light beam will thus be intermittently interrupted as the solid portions of gear 120 between the six slots 130 through 140 pass over the beam. Microprocessor 250 is programmed to count the number of interruptions of the light beam as gear 120 rotates, and is therefore able to calculate the relative rotational position of the gear.

Once microprocessor 250 calculates the correct rotational position of gear 120 and calibrates the rotor as described above, the microprocessor operates motor 100 to position gear 120 in a desired position according to the operation that is to take place. For purposes herein, explanation of the various rotational positions of gear 120, and thus the status of the various fluid flow paths through the valve assembly, will begin with the positions shown in FIG. 6. In FIGS. 6 through 11, the bore numbers refer to the bores in stator 60, and the channel numbers refer to the channels in valve plate 164. It will be appreciated that each position of the valve plate illustrated in FIGS. 6 through 11 corresponds to a stop position for the gear, which is defined by the position the gear is in when a slot in slotted peripheral portion 131 (e.g., 130, 132, 134, etc.) lies directly over the light beam between transmitter 210 and receptor 212 so the beam is uninterrupted. In FIGS. 6 through 11, a slot number is provided in a box in the drawing. When the slot having the number in the box is the slot that lies directly over the light beam, then the stator and valve plate are in the position shown in that drawing.

Figure 6:
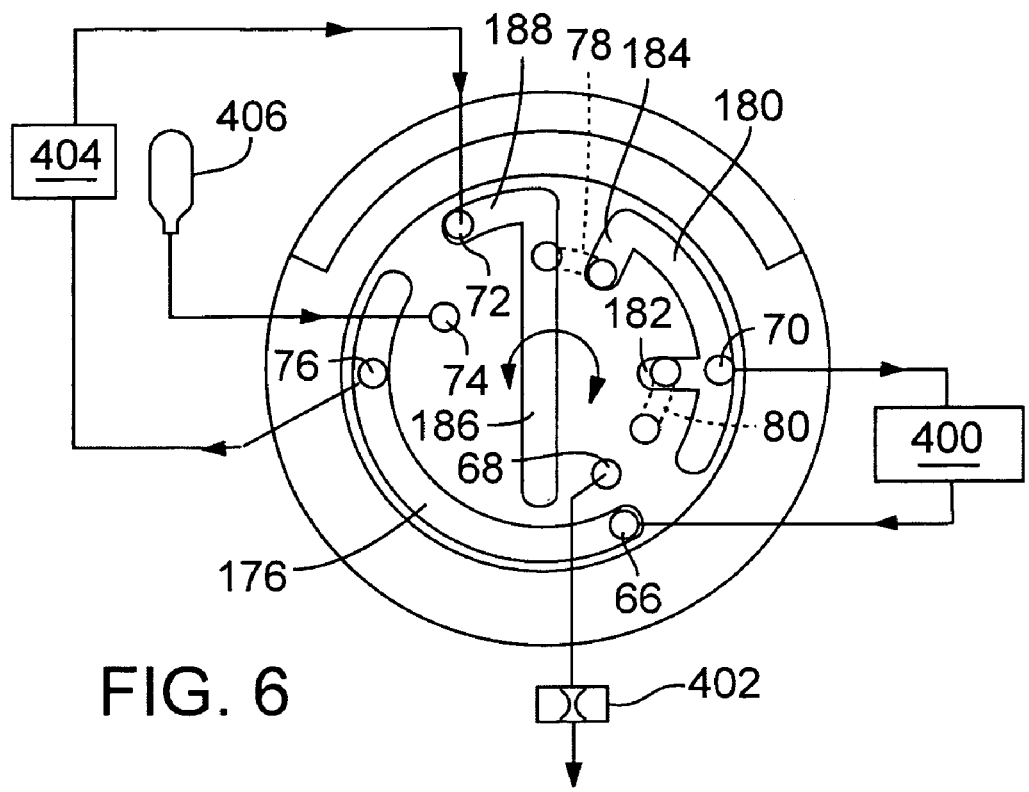
FIGS. 6 through 11 are a series of semi-schematic illustrations of the rotor shown in FIGS. 4A, 4B and 4C according to the present invention shown in six different operational positions to illustrate the fluid connections established with the rotor in each of the six positions.

Reference is now made to FIGS. 6 through 11, which show six operational positions of gear 120 and valve plate 164. Beginning with FIG. 6, in this position sample gas from extractor 404 enters valve assembly 10 through tubing 386, bore 372 and into bore 72. Sample fluid flows into branch channel 188 and channel 186. In this position, channel 78 defines a fluid path between channel 186 and branch 184 of channel 180. Sample gas thus flows out of the valve plate 164, through bore 70 and bore 368 to GC 400. Gas returning from GC 400 flows through bore 66 into channel 176 and is returned to extractor 404 through bore 76. As detailed above, the position of the rotor in FIG. 6 is achieved when slot 138 is over the light beam.

Figure 7:
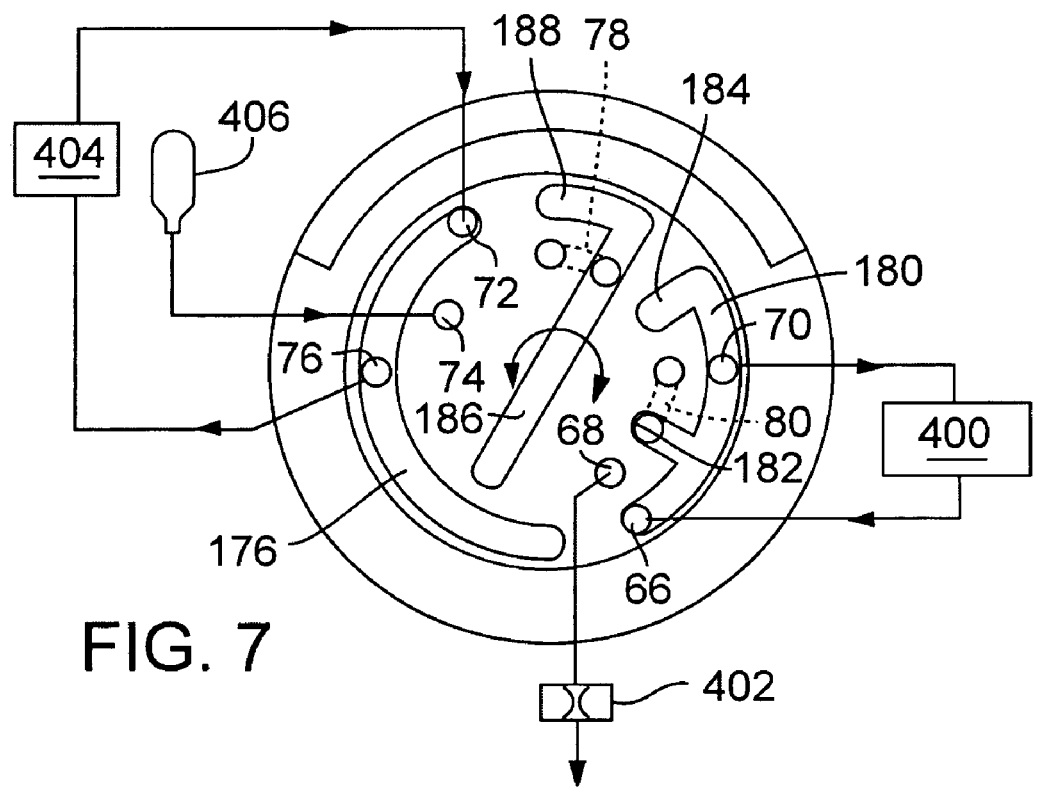

In FIG. 7, gear 120 has been rotated to a second operational position in which the gas flow paths from the extractor 404 and the GC 400 are isolated from one another. In this position, bore 72, which receives gas from extractor 404, is in fluid communication with channel 176. Gas flowing into channel 176 flows out of the valve and back to the extractor via bore 76, which is also in fluid communication with channel 176. Gas from extractor 404 thus flows into valve assembly 10 and is routed directly back to the extractor 404. Similarly, gas from GC 400 enters valve assembly 10 through bore 66 (and associated bores, tubing, etc.), flows through channel 186, and is returned to GC 400 via bore 70. The position of the rotor in FIG. 7 is achieved when slot 136 is over the light beam.

Figure 8:
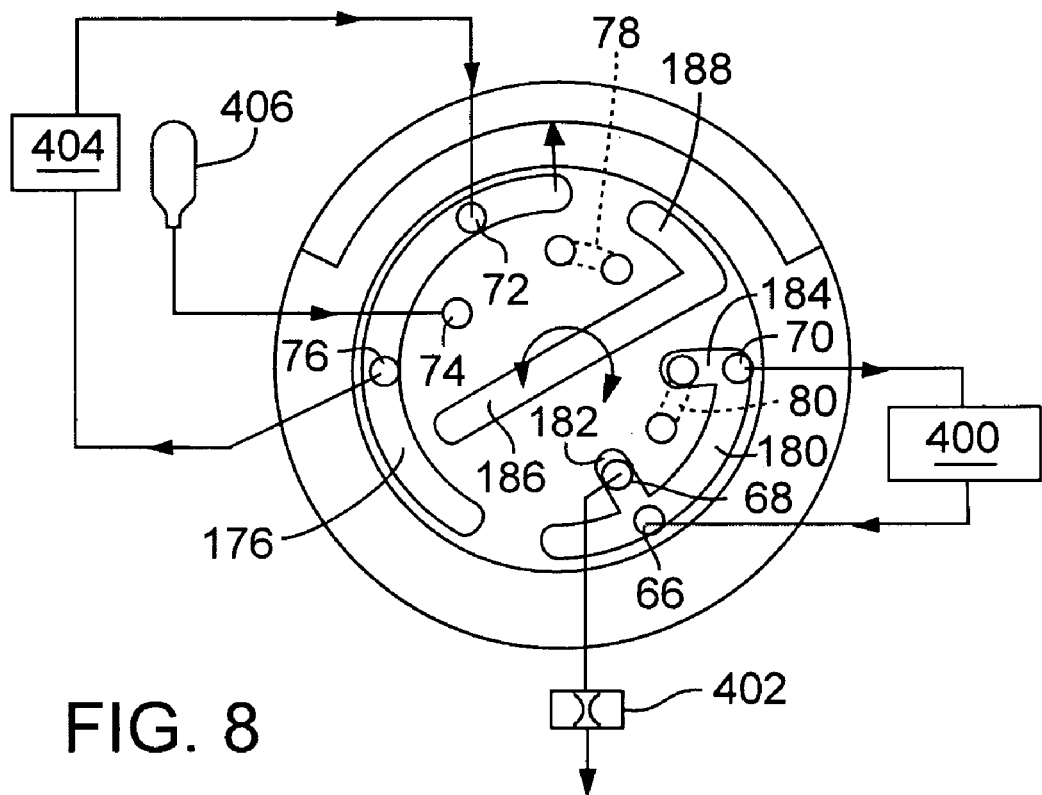

The next sequential position for gear 120 is shown in FIG. 8. Here, valve assembly 10 is set to the venting position. Specifically, gear 120 is rotated under the control over motor 100 until gas from extractor 404 flows through bore 72, through channel 176 and returns to the extractor through bore 76. Simultaneously, gas from both bores 66 and 70, leading to and from GC 400, is allowed to vent through bore 68, which leads to laminar frit restrictor 402. Thus, both bores 66 and 70 in FIG. 8 are in fluid communication with channel 180, and bore 68 is in fluid communication through branch channel 182. The position of the rotor in FIG. 8 is achieved when slot 134 is over the light beam.

Figure 9:
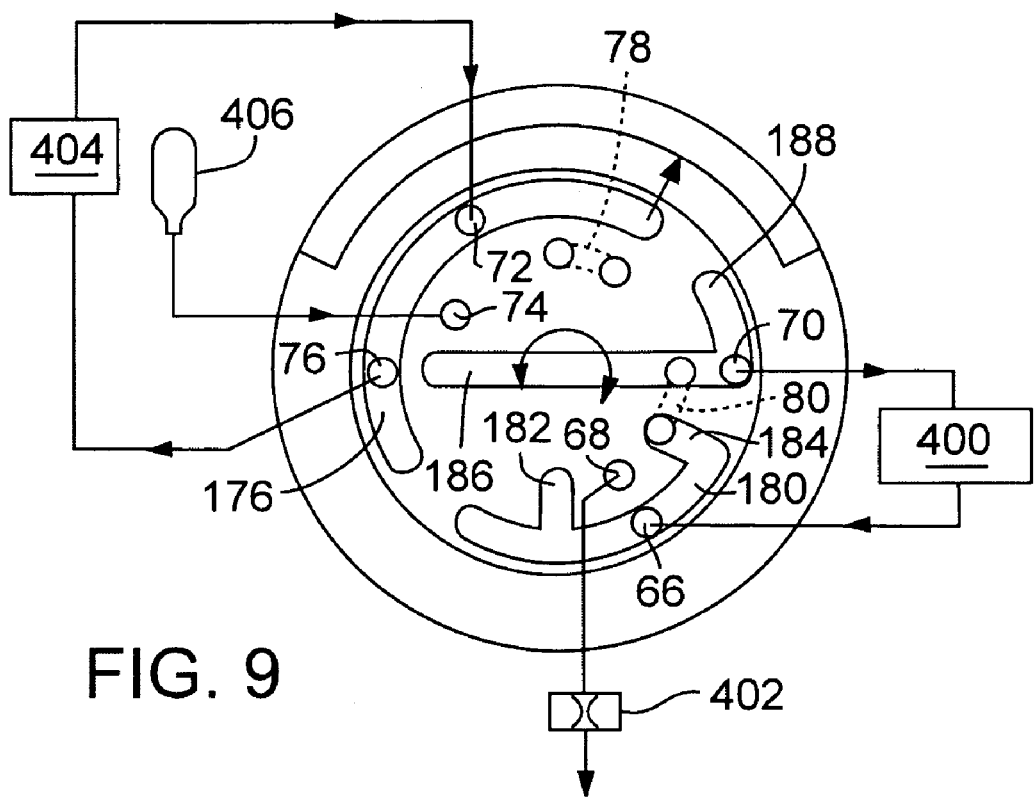

Turning now to FIG. 9, the gear 120 is rotated to a second position in which the extraction gas and GC gas are isolated from one another. The valve assembly in this position is functionally identical to the position shown in FIG. 7. However, in this position the rotary valve is configured to isolate a sample of calibration gas without first passing through the vent position of FIG. 8. The position of the rotor in FIG. 9 s achieved when slot 132 is over the light beam. Specifically with reference to FIG. 9, gas from extractor 404 flows into valve plate 164 through bore 72, which communicates through channel 176 with the outlet through bore 76. Gas is allowed to circulate to and from GC 400 through bore 66, which communicates with channel 180 and through channel 80 via branch channel 184. The opposite end of channel 80 is in communication with channel 186 and bore 70, which defines a return flow path to GC 400.

Figure 10:
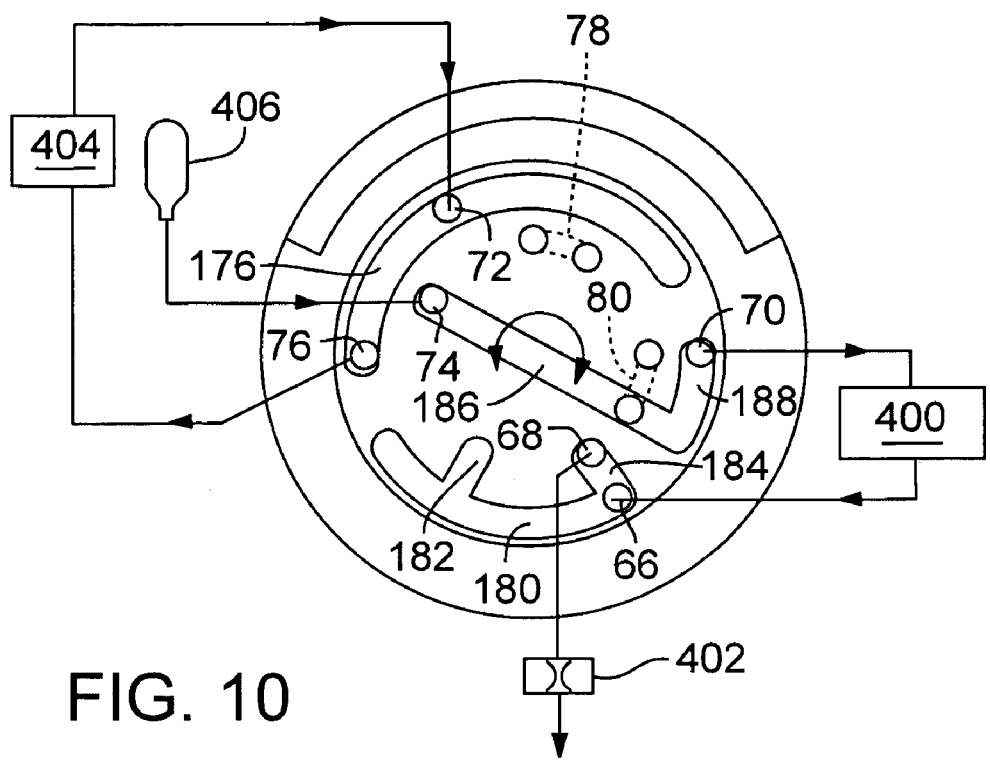

FIG. 10 illustrates the calibration gas circulation position. Here, gas from extractor 404 flows through bore 72, through channel 176 and out bore 76 to return to extractor 404. At the same time, calibration gas from calibration gas supply 406 flows through bore 74 into channel 186 and branch channel 188, exiting to GC 400 through bore 70, which is in communication with branch channel 188. Gas returns from GC 400 through bore 66, which is in communication with bore 68 and thus frit resistor 402 and vent via branch channel 184. The position of the rotor in FIG. 10 is achieved when slot 130 is over the light beam.

Figure 11:
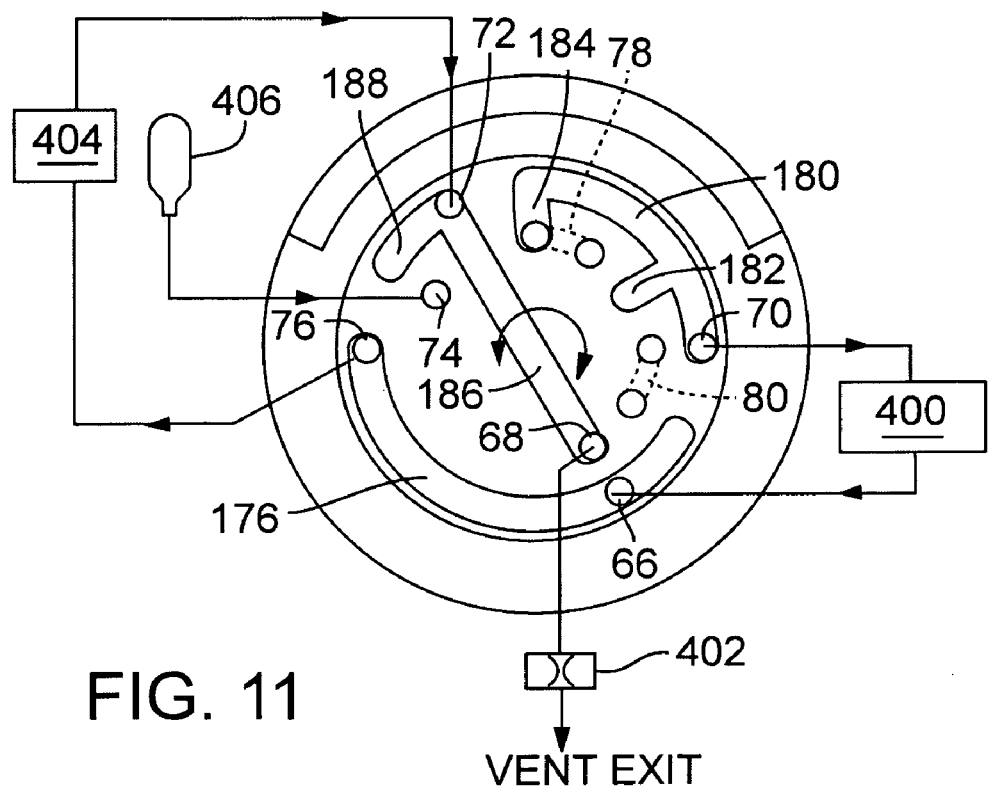

Finally, the extractor pump out position is shown in FIG. 11. In this position the system is purged of gas. A vacuum pump (not shown) may be attached to the vent downstream of frit restrictor 402. When the gear 120 is in the position shown in FIG. 11 and the vacuum pump is activated, gas is evacuated out of the fluid flow paths in the entire system. Alternately, gas may be pumped through the extractor 404 to flush it. And finally, the position of the rotor in FIG. 11 is achieved when slot 140 is over the light beam.

From the foregoing description of the six operational positions of gear 120 and thus valve plate 164, and from FIGS. 6 through 11 it will be appreciated that each operational position of the valve plate defines a unique flow path through valve assembly 10. Thus, as valve plate 164 rotates from one position to another (as shown in FIGS. 6 through 11), a different and unique flow path is defined at each position. The unique flow paths are thus asymmetrically defined by the dual concentric channels 176 and 180, and bisecting channel 186 in valve plate 164, and by the channels 78 and 80 formed in the lower surface 64 of stator 60.

It will be readily appreciated that the rotary valve described above simplifies fluid handling systems by replacing a relatively large number of individual two and three-way binary values that would be required to do the same fluid handling. The invention minimizes the number of active components in the fluid handling system—valves, fittings, tubing, etc.—and thereby decreases the number of possible failure points such as leaks, mechanical and electrical failure points. The rotary valve of the present invention improves reliability and provides positive positional feedback that greatly improves error and failure detection, and the valve reduces material assembly costs. Finally, the valve according to the present invention minimizes interconnecting volumes between system components, which minimizes the amount of fluid cross-contamination and mixing between various components of the system. This improves both accuracy and precision of analytical results.

While the present invention has been described in terms of a preferred embodiment, it will be appreciated by one of ordinary skill that the spirit and scope of the invention is not limited to those embodiments, but extend to the various modifications and equivalents as defined in the appended claims.

We claim:
1. A rotary valve, comprising:
   a stator having plural fluid channels formed therethrough, each fluid channel defining an inlet at a first surface of the stator and an outlet at a second surface of said stator, and wherein the inlets at the first surface are arranged in a first orientation that is different from the orientation of the outlets at the second surface;

a rotary disk having an upper surface with a plurality of flow channels arranged thereon, said upper surface of said disk fluidly sealed against said second surface of said stator, said rotary disk having an effective peripheral edge portion having plural slots therethrough;

a motor for rotating said disk;

a controller programmed to detect the rotational position of said disk relative to said stator and to control said motor to change the rotational position of the disk, said controller including an optical sensor capable of interacting with said slots for determining the position of the rotary disk relative to the stator.

2. The rotary valve according to claim 1 further including at least one channel formed in the second surface of the stator, said at least one channel positioned relative to said rotary disk to define a flow path between said stator and said rotary disk.

3. The rotary valve according to claim 2 including plural channels formed in the second surface of the stator and wherein each channel is positioned relative to said rotary disk to define a flow path between said stator and said rotary disk.

4. The rotary valve according to claim 1 wherein rotation of the rotary disk to a predetermined position establishes a flow path from said inlet, through the associated fluid channel in the stator through an outlet and through a flow channel in the rotary disk.

5. The rotary valve according to claim 4 wherein the flow path continues from the flow path in the rotary disk into an outlet in the stator, through the associated fluid channel and through the associated inlet.

6. The rotary valve according to claim 1 wherein the controller includes calibration means for determining the position of the rotary disk relative to the stator and for rotating said disk to a desired position relative to the stator.

7. The rotary valve according to claim 6 wherein the controller and optical sensor are operable to detect the position of the rotary disk and move the rotary disk to a desired position to establish a desired flow path through said rotary valve.

8. The rotary valve according to claim 1 wherein said rotary disk is housed in a gear and said effective peripheral edge portion comprises a peripheral edge of said gear, said gear having a first peripheral portion that engages said motor to rotate said gear, and wherein said plural slots are in a second peripheral portion.

9. The rotary valve according to claim 8 including biasing means for urging said rotary disk against said second surface of said stator to define the fluid seal therebetween.

* * * * *